(12) United States Patent
Hall et al.

(10) Patent No.: US 9,872,943 B1
(45) Date of Patent: Jan. 23, 2018

(54) PISTOL GRIP SUCTION DEVICE

(71) Applicant: The United States of America, as Represented by the Secretary of the Air Force, Washington, DC (US)

(72) Inventors: Andrew Hall, Gulfport, MS (US); Hampton L McClendon, Niceville, FL (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 15/386,323

(22) Filed: Dec. 21, 2016

Related U.S. Application Data

(63) Continuation-in-part of application No. 14/672,271, filed on Mar. 30, 2015, now abandoned.

(51) Int. Cl.
*A61M 1/00* (2006.01)

(52) U.S. Cl.
CPC ........ *A61M 1/0035* (2014.02); *A61M 1/0041* (2013.01); *A61M 1/0064* (2013.01); *A61M 1/0062* (2013.01)

(58) Field of Classification Search
CPC .............. A61M 1/0043; A61M 1/0064; A61M 1/0039; A61M 1/0062; A61M 16/0463; A61M 16/04; A61M 39/0613; A61B 2217/005; A61B 2217/007; Y10S 604/902
USPC ............. 251/322, 215, 296; 137/606, 315.36
See application file for complete search history.

(56) References Cited

U.S. PATENT DOCUMENTS

| | | | |
|---|---|---|---|
| 1,008,928 A * | 11/1911 | Simmons | F16K 39/024 137/630.14 |
| 1,889,425 A | 11/1932 | Sorensen | |
| 2,449,497 A | 9/1948 | McLeod | |
| 2,524,474 A * | 10/1950 | Randel | F16K 1/24 251/155 |
| 3,065,749 A | 9/1964 | Brass | |
| 3,146,987 A | 9/1964 | Krayl | |
| 3,208,145 A | 9/1965 | Turner | |
| 3,232,578 A | 2/1966 | Cousins | |
| 3,335,727 A | 8/1967 | Spoto | |
| 3,375,828 A | 4/1968 | Sheridan | |

(Continued)

FOREIGN PATENT DOCUMENTS

EP        EP 0199876        5/1986

*Primary Examiner* — Michael R Reid
*Assistant Examiner* — Paul J Gray
(74) *Attorney, Agent, or Firm* — AFMCLO/JAZ; Timothy Barlow

(57) ABSTRACT

A pistol grip suction device comprises a hollow body member having first leg joining second leg at elbow, the legs being generally tubular and disposed approximately 90 degrees apart; a push rod extending through push rod aperture at elbow, the push rod extending into hollow second leg, the push rod having a button on proximal end outside the body, and valve on distal end inside the body; a valve seat disposed within second leg around push rod; valve mounted on the push rod through the valve seat, the suction port having a diameter at least two times the diameter of push rod through suction port; a spring biasing push rod into extended position with respect to second leg such that valve bears against valve seat and closes suction port, wherein a force against button greater than biasing force of spring displaces valve from valve seat and opens suction port.

9 Claims, 7 Drawing Sheets

(56) References Cited

U.S. PATENT DOCUMENTS

| | | |
|---|---|---|
| 3,469,582 A | 9/1969 | Jackson |
| 3,517,669 A | 6/1970 | Buono et al. |
| 3,568,318 A | 3/1971 | Martin |
| 3,610,242 A | 10/1971 | Sheridan |
| 3,645,497 A | 2/1972 | Nyboer |
| 3,834,388 A | 9/1974 | Sauer |
| 3,863,635 A | 2/1975 | Swatman |
| 3,958,566 A | 5/1976 | Furihata |
| 3,965,901 A | 6/1976 | Penny et al. |
| 4,356,823 A | 11/1982 | Jackson |
| 4,430,073 A | 2/1984 | Bemis et al. |
| 4,447,226 A | 5/1984 | Mayoral |
| 4,451,257 A | 5/1984 | Atchley |
| 4,526,573 A | 7/1985 | Lester et al. |
| 4,770,392 A * | 9/1988 | Schmidt .................. F16K 1/24 251/158 |
| 4,776,840 A | 10/1988 | Freitas et al. |
| 5,013,300 A | 5/1991 | Williams |
| 5,337,780 A | 8/1994 | Kee |
| 5,730,727 A | 3/1998 | Russo |
| 5,855,562 A | 1/1999 | Moore et al. |
| 6,875,198 B2 | 4/2005 | Foley |
| 7,611,490 B2 | 11/2009 | Foley |
| 7,811,256 B2 | 10/2010 | Landman et al. |
| 7,918,822 B2 | 4/2011 | Kumar et al. |
| 2001/0044600 A1 | 11/2001 | Elkins |
| 2005/0251093 A1 | 11/2005 | Abou-Kansoul |
| 2007/0005002 A1 | 1/2007 | Millman |
| 2007/0016136 A1 | 1/2007 | Opie |
| 2009/0182275 A1 | 7/2009 | Huddleston |
| 2009/0187146 A1 | 7/2009 | Landman et al. |
| 2009/0275891 A1 | 11/2009 | DiBiasio et al. |
| 2013/0105721 A1* | 5/2013 | Kabel .................. F16K 31/508 251/328 |

* cited by examiner

US 9,872,943 B1

PISTOL GRIP SUCTION DEVICE

RIGHTS OF THE GOVERNMENT

The invention described herein may be manufactured and used by or for the Government of the United States for all governmental purposes without the payment of any royalty.

Pursuant to 35 U.S.C. § 120, this application claims the benefit of and priority to prior filed co-pending non-Provisional application Ser. No. 14/672,271, filed Mar. 30, 2015, entitled "Pistol Grip Suction Flow Valve", and which is expressly incorporated herein by reference.

FIELD OF THE INVENTION

The present invention relates generally to surgical devices, and more particularly, to a pistol grip suction device.

BACKGROUND OF THE INVENTION

During surgery, it is often necessary to suction out accumulated fluids, such as pooled blood. A suction wand is used for such fluid removal wherein the tip of the wand is placed at the spot of the pooled fluid and the surgeon or nurse uses an appropriate control mechanism to open and close a valve associated with the suction wand. The wand is connected to a vacuum source so that when the valve is open, suction is induced through the wand and the fluid is suctioned out of the area of interest. Once the fluid is removed, the valve is closed, inhibiting further suction through the wand. Often the wand is dual-equipped so that the wand is also fluid-flow connected to an irrigation fluid, allowing irrigation of the surgery site as needed.

Such suction control mechanisms are of great assistance during surgery as removal of the fluid with or without prior irrigation is required in order to allow the surgeon to see the surgery site. However, the problem with current suction systems is that the systems are large, bulky, complex, and have an awkward inline grip so that using the device is tricky and not very comfortable for the surgeon or the surgical nurse. Additionally, some current suction systems are non-disposable so that such systems carry the attendant costs of having to be autoclaved between surgeries.

SUMMARY OF THE INVENTION

The present invention overcomes the foregoing problems and other shortcomings, drawbacks, and challenges of existing suction and irrigation devices. While the invention will be described in connection with certain embodiments, it will be understood that the invention is not limited to these embodiments. To the contrary, this invention includes all alternatives, modifications, and equivalents as may be included within the spirit and scope of the present invention.

According to one embodiment of the present invention a suction device includes a hollow body member having a first leg joining a second leg at an elbow, the first leg and the second leg being generally tubular and disposed at approximately 90 degrees from each other; a push rod extending through a push rod aperture at the elbow, the push rod extending into the hollow second leg of the body, the push rod having a button on a proximal end outside the body, and a valve on a distal end inside the body; a valve seat disposed within the second leg around the push rod, the valve seat oriented perpendicular to the longitudinal axis of the second leg, the valve seat having a circular suction port extending therethrough; a valve mounted on the push rod, the valve having a diameter larger than a suction port through the valve seat, the suction port having a diameter at least two times the diameter of the push rod that extends through the suction port; a spring biasing the push rod into an extended position with respect to the second leg such that the valve bears against the valve seat and thereby closes the suction port, wherein a force against the button which is greater than the biasing force of the spring displaces the valve from the valve seat and opens the suction port.

Such a device provides several advantages. First, the 90-degree arrangement of the first and second legs forms a pistol grip-type human interface, which is very easy and natural to hold, aim, and control. In addition, the button on the end of the push rod for actuating the valve is within easy reach of the user's thumb, which is also very easy and natural to control. Further, the diameter of the push rod being so much smaller than the diameter of the suction port of the valve seat permits the valve and pushrod to move laterally, e.g. to the side of the suction port and second leg, to minimize the interference of the size of the push rod within the suction port, so that blood clots or other pieces which are suctioned, e.g. from the surgical site, may pass through the suction port more freely without restricting the suction port.

According to another embodiment of the invention, the suction device further comprises an irrigation port through the wall of the second leg on the same side of the valve seat as the valve. This arrangement provides an advantage in that, when the valve is closed, the irrigation port is not under the influence of the suction source, and an irrigation fluid, e.g. saline solution, may be delivered from the irrigation port, e.g. Luer Lock or Luer taper, to the surgical site via the suction wand without interference to allow for the introduction into or evacuation of the intraabdominal cavity without suction acting on it.

According to a further embodiment of the invention, the face of the valve includes a generally complementary profile to that of the valve seat. Such an arrangement is advantageous in that it may permit the valve to seal the suction port more effectively, and it may encourage the valve to center itself on the valve seat for a more-complete seal. For example, a flat-faced valve may be paired with a flat valve seat; a tapered-faced valve may be paired with a correspondingly-angled valve seat; or a rounded valve may be paired with a correspondingly rounded valve seat. In another example, because the suction port is circular, the device may function properly with valves having a variety of configurations, e.g. flat, tapered, rounded, or other configurations which are symmetric or have a uniform diameter around the push rod.

According to other embodiments, the valve seat and valve may have a variety of different configurations to promote sealing of the valve, e.g. the valve seat may have a planar face perpendicular to the longitudinal axis of the second leg that bears the face of the valve under the influence of the biasing spring; the valve seat may have an inwardly-tapered face that draws the valve into a centered position on the suction port under the influence of the biasing spring; the circumference of the valve may include a rounded edge that generally complements a rounded groove around the suction port of the valve seat; and/or the valve may be a ball or hemisphere that bears against a valve seat having a planar, tapered, or rounded configuration to seal the suction port. Each of these configurations is advantageous in that they may promote effective and complete sealing of the suction port, may promote the centering of the valve within the suction port of the valve seat, and may promote fluid flow through the second leg and suction port.

According to a further embodiment of the invention, the push rod is movable within the suction port to contact the edges of the suction port. This arrangement is advantageous in that it may increase the increase the effective area of the suction port when the push rod is in contact with one edge of the suction port, which may allow larger pieces to be drawn through the suction port, and such an arrangement may increase the diameter of the suction port to reduce resistance and allow larger particulate matter to be drawn through the suction port.

According to another embodiment of the invention, the suction device may further comprise a suction wand which may be removably attached to the second leg opposite the push rod aperture. Various types and sizes of wands may be attached, depending on the particular needs of the surgery.

There are numerous addition advantages to the invention. The claimed arrangement creates a parallel flow along the central axis of the device, i.e. inside the second leg and along/around the push rod, which enables the pistol-grip configuration, making for much more intuitive and ergonomic use. The valve on the end of the push rod may lie on the valve seat in the middle of the second leg of the device. This valve may allow for continued pressurization at one side of the valve, e.g. for irrigation, and suction on the other side of the valve when the valve is in a closed position. The suction port may be larger than the norm in order to allow for movement of the push rod to the top, bottom or side of the suction port in order to provide an increased diameter of the suction port. The seal between the valve and the valve seat does not need to be perfect, and the spring may need to just strong enough to draw the valve toward the valve seat, because the force of suction draws those parts closer together to effect a seal. The external spring may provide additional stabilization of the push rod to ensure the valve is in a closed position, and the button on the end of the push rod may be deflected to induce lateral motion of the push rod and valve inside the second leg. The push rod aperture, which passes through the elbow, may be just big enough to allow the push rod to pass through the wall of the elbow, or the push rod aperture may be made large enough to allow the push rod to be deflected, i.e. side-to-side play, by manipulating the button on the proximal end of the push rod, e.g. with the user's thumb. There is only one moving part in the device, and no complex seals. The tapered suction connection may allow for generic suction tubing connections, and a modular threaded second leg may allow the use of generic suction cannula connections.

The device may be used in various surgical procedures, e.g. laparoscopic surgery. In a laparoscopic procedure, the abdominal cavity is filled with carbon dioxide and the pressure is increased to 15 mm Hg above atmospheric, which provides room to work in the abdomen. The device may allow for the removal of fluids/blood by opening up a valve and introducing suction. A cannula at the end of the device allows for directed suction and without the loss of the insufflating gas. An irrigation port on distal side of the device, i.e. on the same side of the valve seat as the valve, allows introduction of other fluids/interventions when the valve is in the closed position.

This device is unique in that known prior art devices use a valve where the direction of flow is perpendicular to the valve and not parallel. This forces the user to hold the device in a manner which is not comfortable for prolonged, controlled use, i.e. similar to a trumpet.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Figure 1:
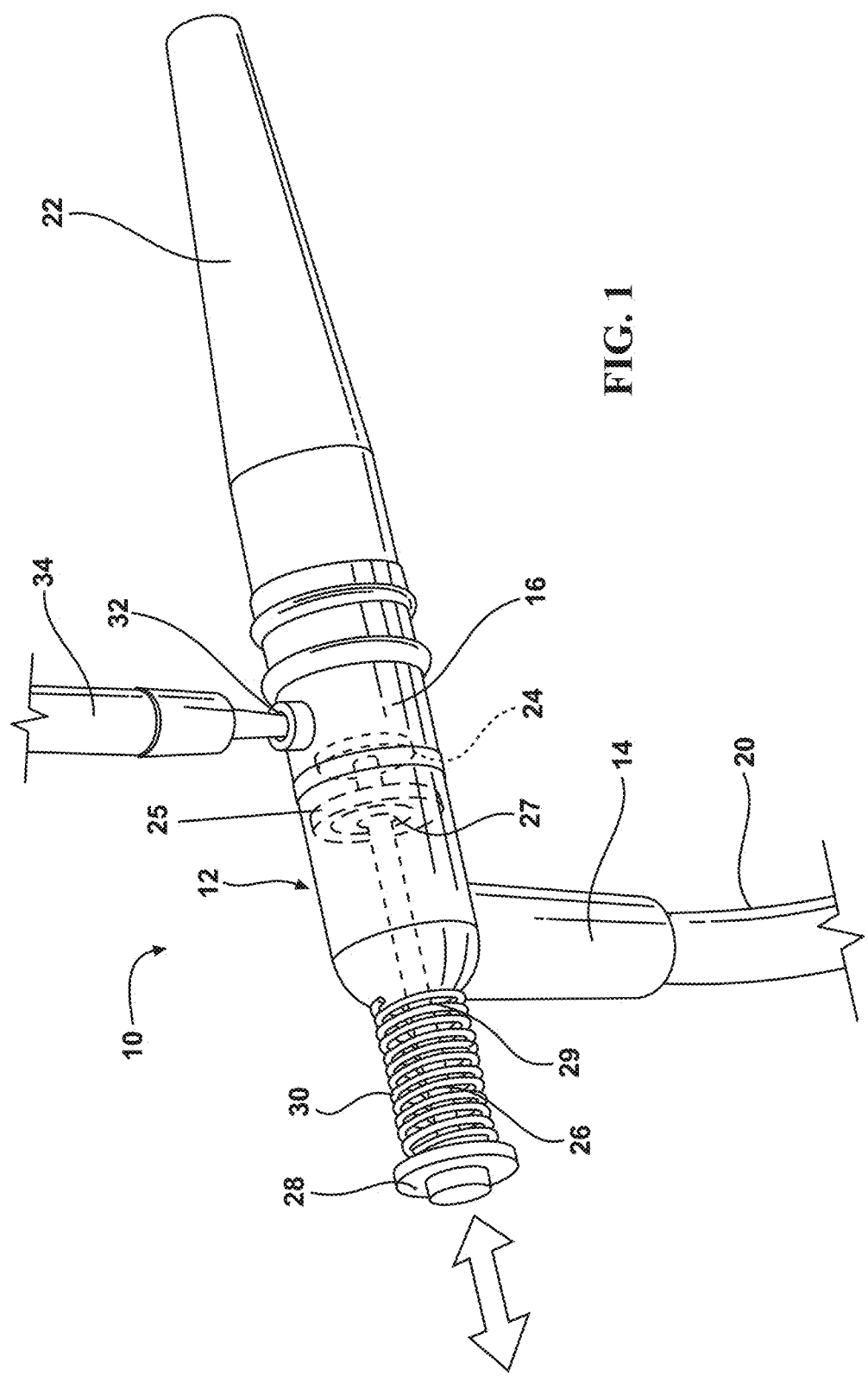
FIG. 1 is a perspective view of a pistol grip suction device connected to a suction hose, according to an embodiment of the invention.
Figure 2:
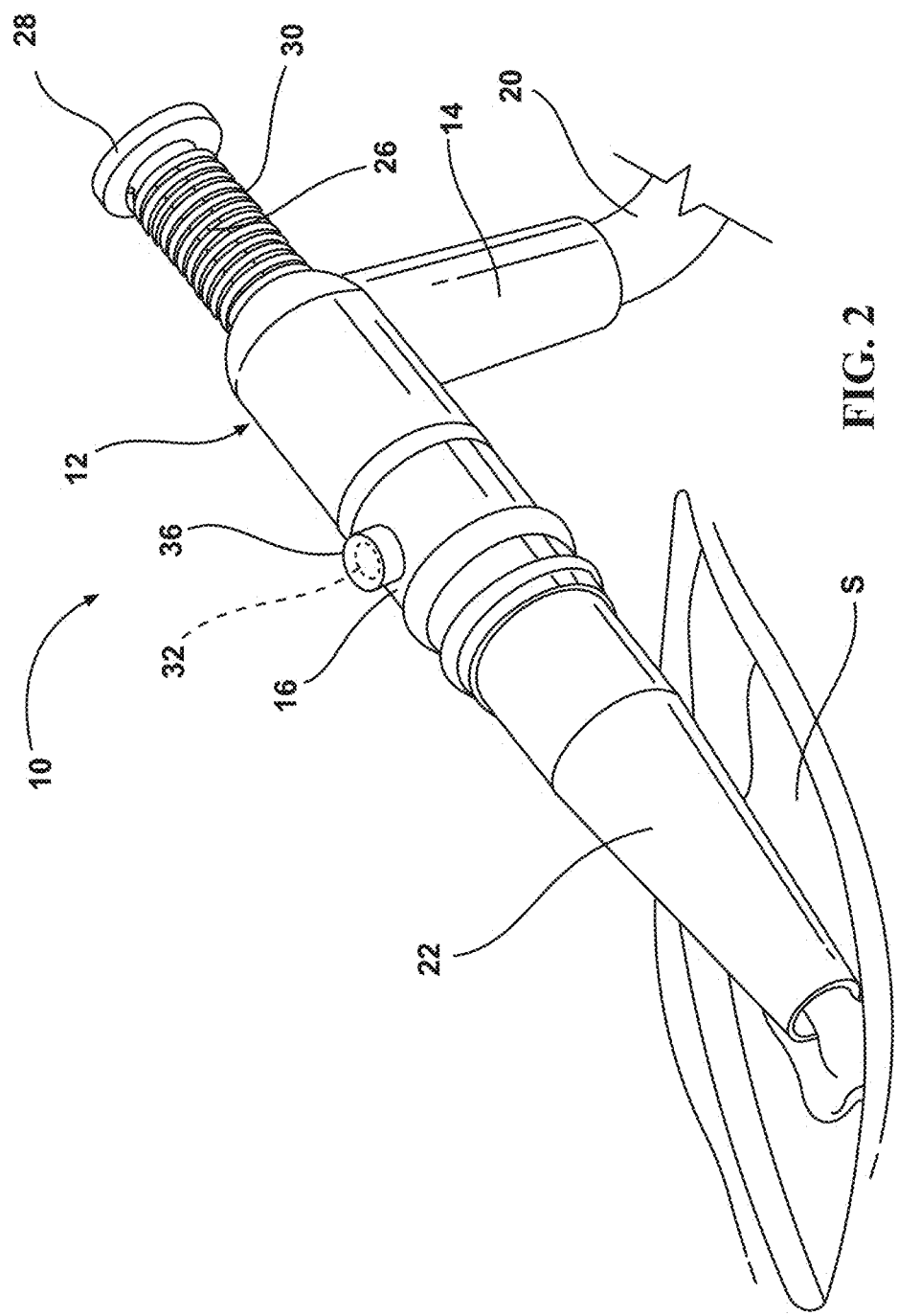
FIG. 2 is a perspective view of a pistol grip suction device connected to a suction hose, according to an embodiment of the invention.
Figure 3:
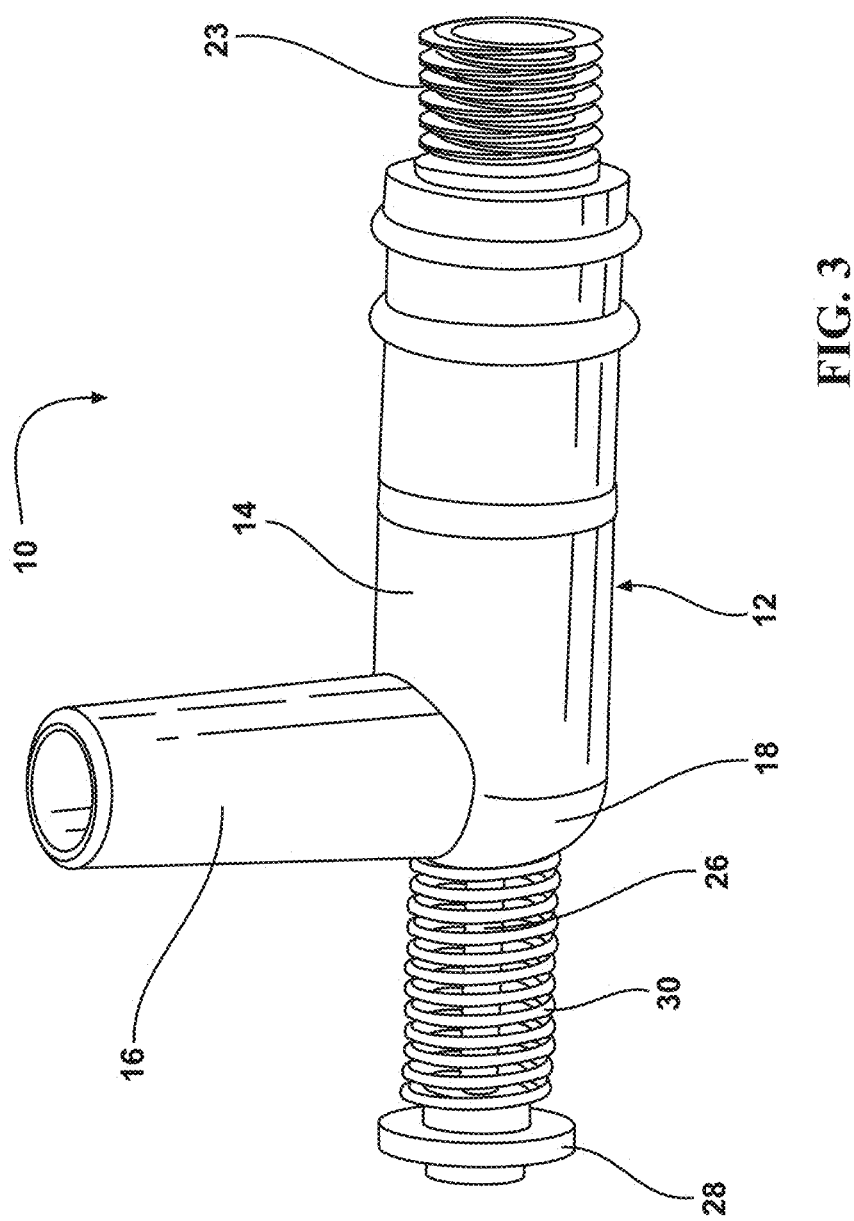
FIG. 3 is a perspective view of a pistol grip suction device with the suction wand removed, according to an embodiment of the invention.

Referring now to FIGS. 1-3, it is seen that pistol grip suction control device of the present invention, generally denoted by reference numeral 10, is comprised of a body member 12 that has a first leg 14 and a second leg 16 that is joined to the first leg 14 at an elbow 18. The elbow 18 may be approximately 90 degrees, as illustrated, or the elbow may be any other angle or configuration which enhances the grip or handling qualities of the device. As illustrated, a suction hose 20 may be removably connected to the end of the first leg 14. The hose 20 may provide a flow of fluid through the device when the other end of the hose is connected to a vacuum source in typical fashion. The first leg 14 may include a standard taper to allow common and standard suction hoses or other suction equipment to be attached. A suction wand 22 or other standard suction accessories may be threadably 23 or otherwise attached to the distal end 38 of the second leg 16. When attached to the second leg 16 of the device 10, the suction wand 22 may be placed at a surgery site S (see FIG. 2) for suctioning fluid and/or particulate matter therefrom and/or irrigating the surgery site S with an appropriate irrigation fluid, as more fully described below.

A valve 24, such as the illustrated choke valve 24, may be disposed within the second leg 16 such that a push rod 26 is connected to the valve 24, with the push rod 26 extending out from the proximal end 37 of the second leg 16 at the elbow 18, through the push rod aperture 29. An appropriate button 28 may be located on the end of the push rod 26. The push rod 26 may be spring-loaded such that a spring 30 abuts the outer surface of the second leg 16 at the elbow 18 around the push rod aperture 29, and the spring 30 may also abut the underside of the button 28. In a normally relaxed state, the push rod 26 is maximally extended out from the second leg 16 through the push rod aperture 29 via the bias of the spring 30, such that the valve 24 is in a closed position against the valve seat 25 so that fluid does not flow past the valve 24 and through the suction port 27 in the valve seat 25.

Figure 4:
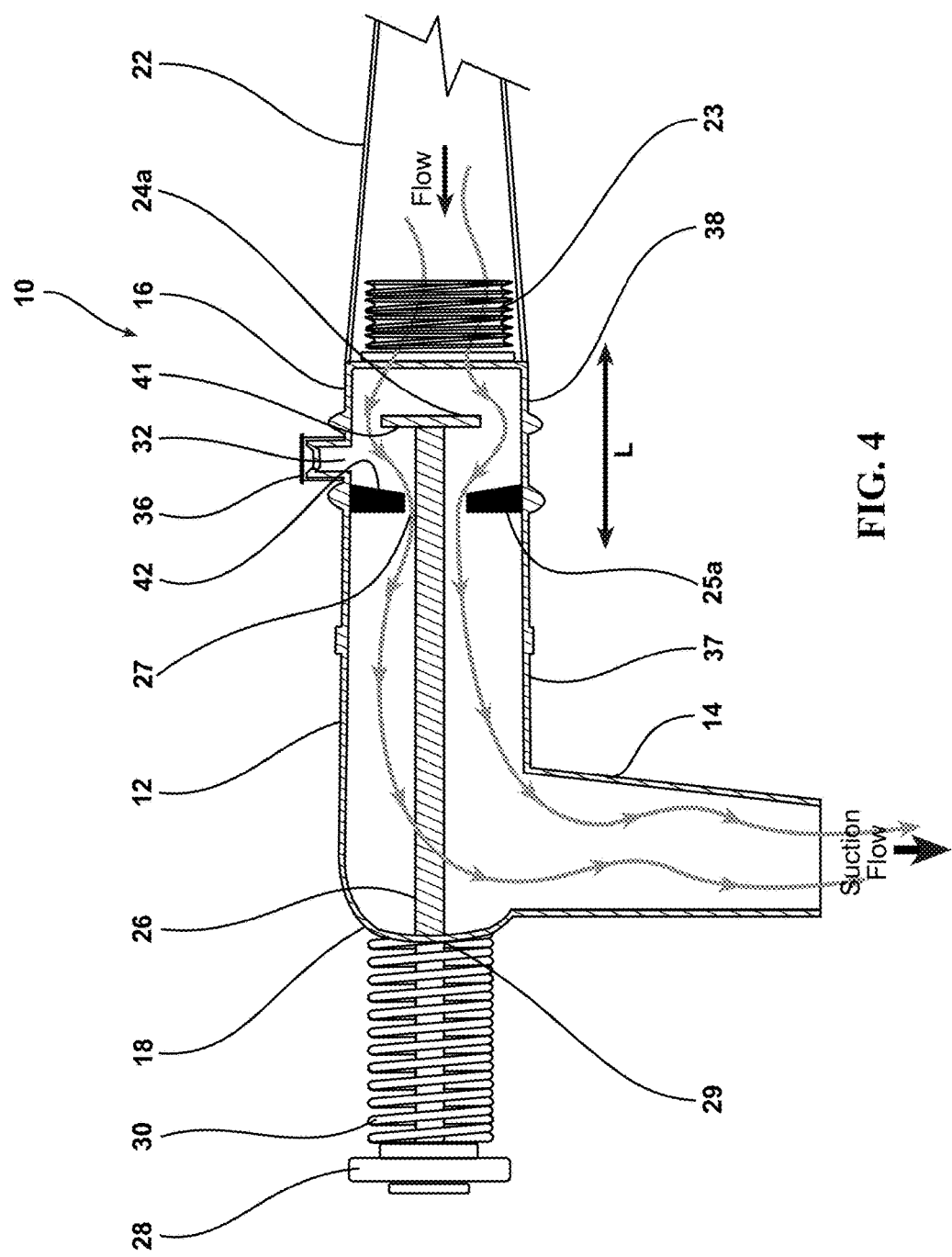
FIG. 4 is a sectional view of a pistol grip suction device with the suction port open, according to an embodiment of the invention.
Figure 5:
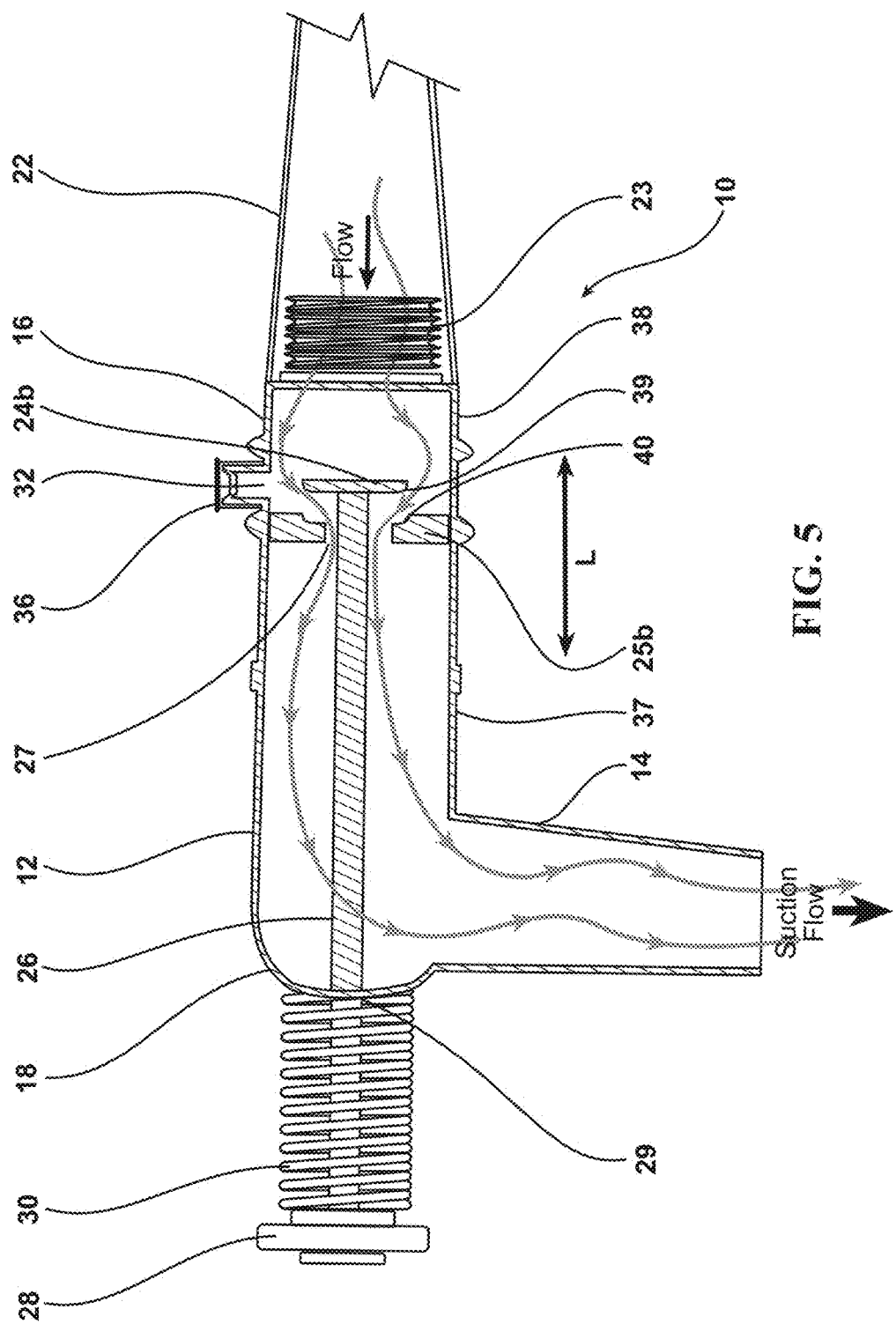
FIG. 5 is a sectional view of a pistol grip suction device with the suction port open, according to an embodiment of the invention.
Figure 7:
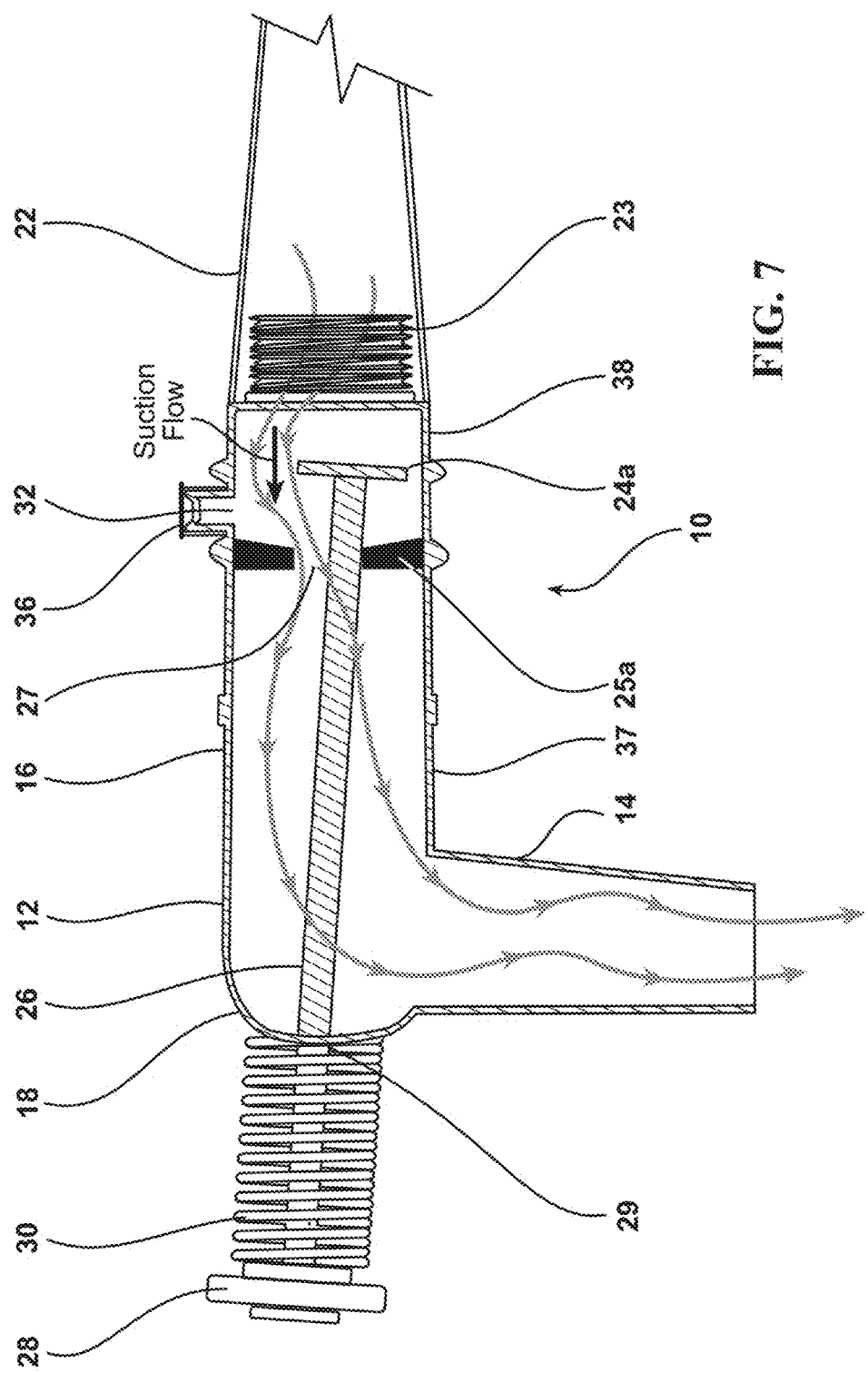
FIG. 7 is a sectional view of a pistol grip suction device with the suction port open and push rod deflected to bottom of suction port, according to an embodiment of the invention.

As the push rod 26 is depressed into the second leg 16, against the force of the spring 30, the valve 24 is displaced away from the valve seat 25 so that fluid may flow through the suction port 27, as depicted in FIGS. 4, 5 and 7. When the push rod 26 is released, the spring 30 biases the push rod 26 back to its normally relaxed, fully extended state, thereby once again terminating flow through the suction port 27.

An irrigation port 32, which may include a Luer lock or Luer taper, may be located on the second leg 16 of the body member 12 such that a Luer lock or Luer taper equipped syringe 34 or other source of irrigation fluid may be removably attached to the irrigation port 32 for supplying irrigation fluid to the surgical site S. The irrigation port 32 may be closed with an irrigation port cap 36 when not in use. The irrigation port 32 may be located on the distal end 38 of the second leg 16 such that the valve seat 27 is between the irrigation port 32 and the first leg 14. This arrangement ensures that, when the suction port 27 is closed, any suction from the first leg 14 will not disturb the flow of irrigation fluid from irrigation port 32 into surgery site S.

In order to use the pistol grip suction and irrigation device 10 of the present invention, a wand 22 may be attached to the distal end of the second leg 16 while the end of the first leg 14 is fluid flow connected to a vacuum source via suction hose 20. The vacuum source may be activated. As the surgeon or nurse needs suction at a particular site S, the end of the wand 22 is placed at the site S. The user grips the pistol grip suction and irrigation device 10 in pistol grip fashion by wrapping his or her fingers around the first leg 14. The user can then use his or her thumb on the gripping hand to depress the button 28 of the push rod 26 as needed. When suction is required, the user depresses the button 28 of the push rod 26 a desired amount in order to get the desired amount of suction at the end of the wand 22. When suction is no longer required, the button 28 of the push rod 26 is released, allowing the push rod 26 to return to its normally relaxed state via the bias of the spring 30, thereby closing the suction port 27 and terminating suction. If irrigation of the site S is required, with the suction port 27 closed, then the fluid-bearing syringe 34 or other source of irrigation fluid is inserted into the irrigation port 32 and locked in place, and the fluid is discharged into the irrigation port 32 in a fashion such that the irrigation fluid flows through the wand 22 to the surgical site S. Thereafter, the syringe 34 may be removed and the irrigation port 32 capped, allowing for further suctioning, as needed.

Although the pistol grip suction control valve 10 may be cleaned and sterilized after use, due to its simple and straightforward construction, it may be viewed as being more cost effective and safer to simply dispose of the unit after usage and use a new pistol grip suction device 10 for a subsequent surgery.

The body member 12, the push rod 26, the valve 24 and the spring 30 may be made from any appropriate biocompatible plastic or surgical steel or other similar material, or combinations of materials.

FIGS. 4-7 illustrate sectional views of various internal arrangements of the pistol grip suction device 10. FIG. 4 illustrates an arrangement of the device 10 wherein the face 42 of the valve seat 25a is inwardly tapered. The valve seat 25a may be arranged perpendicular to the longitudinal axis L of the second leg 16. When the spring 30 biases the pushrod 26 and valve 24a against the valve seat 25a, the inwardly tapered surfaces will tend to center the valve 24a on the valve seat 25a, which closes the suction port 27 of the valve seat 25a. As illustrated, however, the button 28 is depressed such that the valve 24a is not against the valve seat 25a, and the suction port 27 is open. The suction source (not depicted) creates a flow (see arrows) and draws fluids through the suction wand 22, into the distal side of the second leg 16, past valve 24a, through suction port 27 into proximal side 37 of second leg 16, into first leg 14, and toward the suction source.

FIG. 5 illustrates an arrangement of the device 10 wherein the face 41 of valve 24b is general flat but with a rounded edge 39 that generally complements a rounded groove 40 around the suction port 27 of the valve seat 25b. By 'generally complements' it is understood that the rounded feature of the valve 24b and the groove of the valve seat 25b are not necessarily an exact match, but are close enough to promote the positive sealing and closure of the device 10 such that there is no fluid flow through the suction port 27. The valve seat 25b may be arranged perpendicular to the longitudinal axis L of the second leg 16. Similar to the embodiment illustrated in FIG. 4, when the spring 30 biases the pushrod 26 and valve 24b against the valve seat 25b, the rounded surfaces will tend to center the valve 24b on the valve seat 25b, which closes the suction port 27 of the valve seat 25b. As illustrated, however, the button 28 is depressed such that the valve 24b is not against the valve seat 25b, and the suction port 27 is open. The suction source (not depicted) creates a flow (see arrows) and draws fluids through the suction wand 22, into the distal side of the second leg 16, past valve 24b, through suction port 27 into proximal side 37 of second leg 16, into first leg 14, and toward the suction source.

Figure 6:
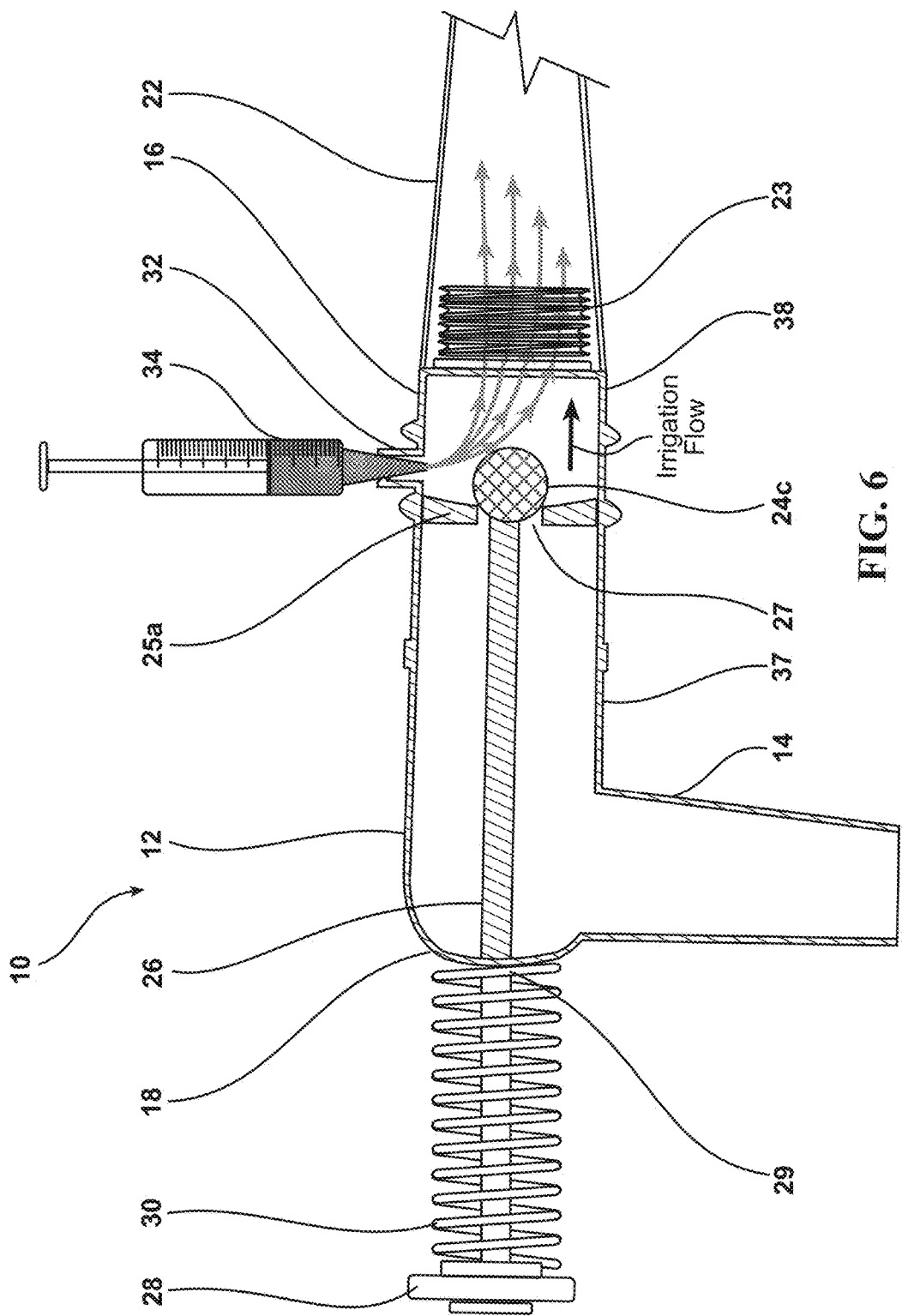
FIG. 6 is a sectional view of a pistol grip suction device with the suction port closed, according to an embodiment of the invention.

FIG. 6 illustrates an arrangement of the device 10 wherein the valve 24c is a ball that mates with the suction port 27 of the valve seat 25. By 'generally complements' it is understood that the ball valve 24c and the valve seat 25 are not necessarily an exact match, but are close enough to promote the positive sealing and closure of the device 10 such that there is no fluid flow through the suction port 27. The valve seat 25 may be arranged perpendicular to the longitudinal axis L of the second leg 16. Similar to the embodiment illustrated in FIGS. 4-5, when the spring 30 biases the pushrod 26 and valve 24c against the valve seat 25, the rounded surfaces will tend to center the ball valve 24c on the valve seat 25, which closes the suction port 27 of the valve seat 25. As illustrated, the button 28 is not depressed such that the ball valve 24c is not against the valve seat 25, and the suction port 27 is closed such that there is no fluid flow through the suction port 27. Instead, a syringe 34 is coupled to the irrigation port 32 and irrigation fluid (see arrows) is being delivered into the distal side of the second leg 16, and into the suction wand 22, toward the surgery site S.

FIG. 7 illustrates an arrangement of the device 10 wherein push rod 26 is deflected toward the bottom of the suction port 27 such that it bears against the valve seat 25a. The deflection of the push rod 26 effectively creates a suction port 27 having an opening capable of allowing larger particular matter to pass through the suction port 27. The valve seat 25a may be arranged perpendicular to the longitudinal axis L of the second leg 16. As illustrated, the button 28 is depressed inward to unseat valve 24a from the valve seat 25a, and the button 28 is pressed slightly upward such that push rod 26 is forced downward against the valve seat 25a. In this configuration, the suction port 27 offers the largest possible opening. The suction source (not depicted) creates a flow (see arrows) and draws fluids through the suction wand 22, into the distal side of the second leg 16, past valve 24a, through suction port 27 into proximal side 37 of second leg 16, into first leg 14, and toward the suction source.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A pistol grip suction device comprising:
   a hollow body member having a first leg joining a second leg at an elbow, the first leg and the second leg being generally tubular and disposed at an angle from each other;
   a push rod extending through a push rod aperture at the elbow, the push rod extending into the hollow second leg of the body, the push rod having a button on a proximal end outside the body, and a valve on a distal end inside the body;
   a valve seat disposed within the second leg around the push rod, the valve seat oriented perpendicular to the longitudinal axis of the second leg, the valve seat having a circular suction port extending therethrough;
   the valve mounted on the push rod, the valve having a diameter larger than the suction port through the valve seat, the suction port having a diameter at least two times greater than the diameter of the push rod that extends through the suction port, the push rod being radially-movable within the suction port to contact the edges of the suction port;
   a spring biasing the push rod into an extended position with respect to the second leg such that the valve bears against the valve seat and thereby closes the suction port, wherein a force against the button which is greater than the biasing force of the spring displaces the valve from the valve seat and opens the suction port.

2. The pistol grip suction device of claim 1, further comprising:
   an irrigation port through a wall of the second leg on the same side of the valve seat as the valve.

3. The pistol grip suction device of claim 1, wherein the valve includes a complementary profile to that of the valve seat.

4. The pistol grip suction device of claim 1, wherein the valve seat has a planar face perpendicular to the longitudinal axis of the second leg that bears against the valve under the influence of the biasing spring.

5. The pistol grip suction device of claim 1, wherein the valve seat has an inwardly-tapered face that draws the valve into a centered position on the suction port under the influence of the biasing spring.

6. The pistol grip suction device of claim 1, wherein the circumference of the valve includes a rounded edge that generally complements a rounded groove around the suction port of the valve seat.

7. The pistol grip suction device of claim 1, wherein the valve is one of a ball or hemisphere that bears against the valve seat to seal the suction port.

8. The pistol grip suction device of claim 7, wherein the valve seat includes a planar face perpendicular to the longitudinal axis of the second leg, which planar face bears the valve when the suction port is closed.

9. The pistol grip suction device of claim 1, further comprising:
   a suction wand removably attached to the second leg opposite the push rod aperture.

\* \* \* \* \*